(12) United States Patent
Kodama et al.

(10) Patent No.: US 7,862,521 B1
(45) Date of Patent: Jan. 4, 2011

(54) UTERINE CONTRACTION SENSING SYSTEM AND METHOD

(75) Inventors: Roy K. Kodama, Thousand Oaks, CA (US); Oscar Garza, Ventura, CA (US); Robert Guthrie, Ventura, CA (US); Andrew Gilman, Ventura, CA (US)

(73) Assignee: Parker-Hannifin Corporation, Cleveland, OH (US)

( * ) Notice: Subject to any disclaimer, the term of this patent is extended or adjusted under 35 U.S.C. 154(b) by 1460 days.

(21) Appl. No.: 11/123,862

(22) Filed: May 6, 2005

Related U.S. Application Data

(63) Continuation-in-part of application No. 10/113,890, filed on Mar. 27, 2002, now abandoned.

(51) Int. Cl.
*A61B 5/103* (2006.01)
*A61B 5/117* (2006.01)

(52) U.S. Cl. ...................................... 600/588; 600/591

(58) Field of Classification Search .................. 600/587, 600/588, 591, 595
See application file for complete search history.

(56) References Cited

U.S. PATENT DOCUMENTS

| 4,873,986 A | 10/1989 | Wallace |
| 4,989,615 A | 2/1991 | Hochberg |
| 5,070,888 A | 12/1991 | Hon et al. |
| 5,195,536 A | 3/1993 | Silva et al. |
| 5,218,972 A | 6/1993 | Gorsuch et al. |
| 5,224,490 A | 7/1993 | Allen et al. |
| 5,289,827 A | 3/1994 | Orkin et al. |
| 5,634,476 A | 6/1997 | Orkin et al. |
| 5,661,245 A | 8/1997 | Svoboda et al. |
| 5,879,293 A | 3/1999 | Hojaiban et al. |

*Primary Examiner*—Max Hindenburg
*Assistant Examiner*—Jonathan M Foreman
(74) *Attorney, Agent, or Firm*—Howard N. Sommers

(57) ABSTRACT

The present invention provides a system for enabling the sensing of changes in pressure in response to uterine muscle tone changes relating to contractions, and for enabling the evaluation of contractions based thereon. The system enables a portion thereof to effectively and efficiently project at least partially below the non-compressed abdominal surface, and provides electrical isolation of the system elements. It enables ease of use and enhanced patient comfort. It also enables maximized sensitivity and minimized system loading retention pressure.

10 Claims, 5 Drawing Sheets

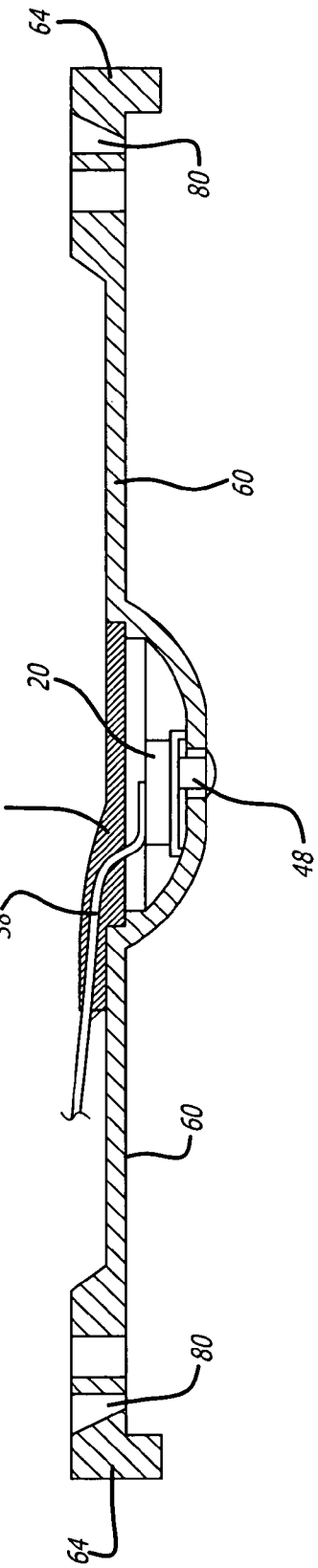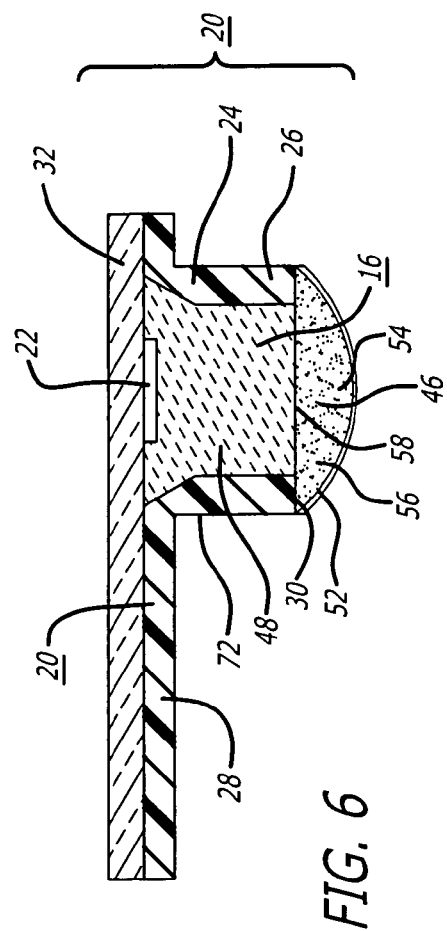

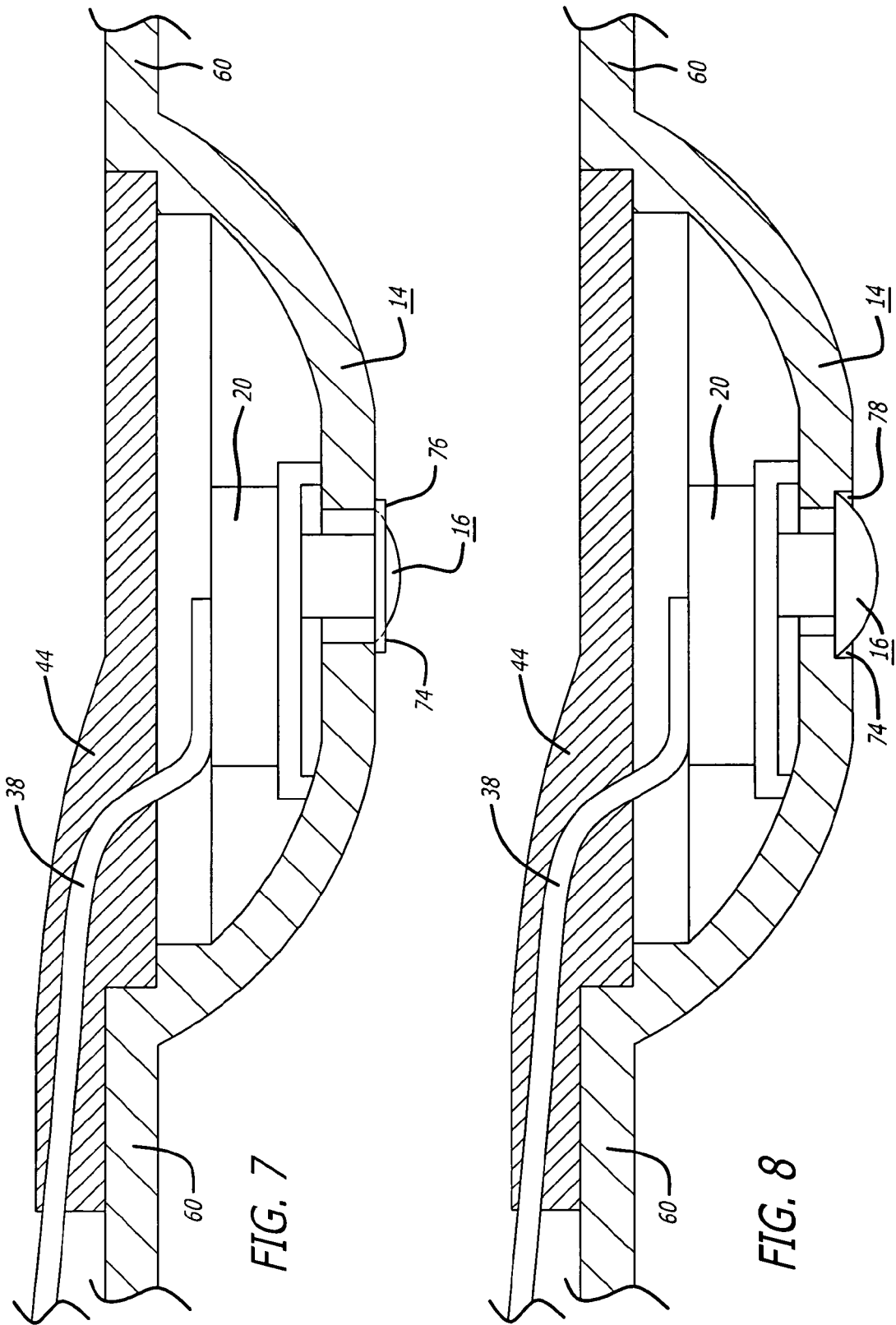

UTERINE CONTRACTION SENSING SYSTEM AND METHOD

CROSS-REFERENCE TO RELATED APPLICATION

This application is continuation-in-part of a application Ser. No. 10/113,890 filed on Mar. 27, 2002 now abandoned.

BACKGROUND OF THE INVENTION

1. Field of the Invention

This invention is generally related to devices for sensing uterine contractions during labor, and more particularly, to a system and method for sensing the frequency and duration of contractions, and for estimating the relative intensity thereof.

2. General Background and State of the Art

During a contraction, the muscle tone of the uterus increases. This increase in muscle tone applies pressure to the abdomen. The abdomen hardens and the shape changes due in part to the muscles surrounding the anterior ligament of the uterus pulling the abdomen forward.

It is known to provide systems for estimating the force of uterine contractions during labor, generally known as tocodynamometers, which sense, in relative terms, the increase and decrease in abdominal pressure relating to uterine contractions, and enable evaluation thereof. Such systems have typically included a cantilevered beam as a sensor, and a button as a force collector, which is connected to the sensor by a link pin. The output from the system is sent to a fetal monitor, which displays the relative pressure in the form of a digital reading and strip chart recording. The clinician, in reviewing the chart recording, can observe the progress of labor in terms of contraction frequency and duration, and can obtain a rough indication of the relative intensity of the contractions.

However, such systems are relatively large and bulky, require relatively large devices to hold them in place, and are expensive. Further, they are relatively difficult to use, require relatively high belt tension which is uncomfortable, and tend to migrate and require repositioning.

It would therefore be desirable to provide a sensing system which would sense the frequency and duration of uterine contractions during labor, and estimate the relative intensity thereof, in a manner which would maximize the sensitivity of the system and enhance ease of use and patient comfort. It would further be desirable to enable unique leveraging thereof, for loading onto the abdomen with the exertion of substantially minimal retention pressure. It would still further be desirable to enable support of the system so as to project into the abdomen wall to efficiently reside below the non-compressed abdominal surface. Moreover, it would be desirable to provide electrical isolation of the patient, to prevent the flow of current thereto Therefore, there has been identified a continuing need to provide a sensing system which will effectively sense uterine contraction frequency and duration during labor, for enabling efficient estimation of the relative intensity thereof.

INVENTION SUMMARY

Briefly, and in general terms, the present invention, in a preferred embodiment, by way of example, is directed to a system for sensing the frequency and duration of uterine contractions during labor and estimating the relative intensity thereof. The system is able to sense changes in pressure in response to uterine muscle tone changes relating to contractions, and to enable a fetal monitor to be connected thereto for evaluation of contractions. The system includes a pressure sensor, for sensing changes in pressure responsive to uterine muscle tone changes, positionable against the exterior abdominal wall proximate the uterine muscle, connectable to a fetal monitor for evaluation of contractions during labor, and supportable so as to project into the abdominal wall to reside at least partially below the non-compressed surface of the abdomen. The system also includes a supporting element, for supporting the pressure sensor such that the pressure sensor projects into the abdominal wall to reside at least partially below the non-compressed surface of the abdomen.

In accordance with another aspect of the invention, the supporting element may include extending portions which extend from the opposed sides thereof, which include attachment portions and attachment points at the opposed ends thereof, for enabling a securing element to be connected to the attachment portions and attachment points in the opposed ends of the extending portions, to secure the system about the abdomen. The system further includes a force collector, which includes edges thereof. The leveraging provided by the extending portions including the attachment portions, and a leveraging ratio of the distance from the attachment points through the force collector edges, is sufficiently flexible to enable deflection with the tension exerted by the securing element thereon, so that the supporting element conforms to the natural curvature of the abdomen.

In another aspect of the invention, the force collector is secured to the pressure sensor, and a protective cover extends over the force collector for protectively covering the force collector. The protective cover may have a vent hole therein, for enabling the venting of trapped air therethrough, and for preventing zero shifts which might occur due to thermal effects. The protective cover enables the force collector to slide over the patient's skin, and prevents sticking upon repositioning thereof, which might otherwise cause negative pressure readings when the pressure cover is unloaded and returns to its natural state.

In still another aspect of the invention, the force collector includes an outer section and an inner section, and the coefficient of thermal expansion of the outer section of the force collector is substantially similar to the coefficient of thermal expansion of the inner section of the force collector, to prevent a zero shift in the pressure reading as the system warms on the patient's skin.

In a further aspect of the invention, the force collector further includes an outer portion of the outer section, and an inner portion of the outer section, and the average thickness of the outer portion of the outer section of the force collector is less than the average thickness of the inner portion of the outer section of the force collector, to overcome slight differences in coefficients of thermal expansion of the outer portion and the inner portion of the outer section of the force collector. The outer portion of the outer section is retained firmly against a non-moving surface, keeping the thickness of the outer portion down in this area, and allowing the outer section to move more freely over the inner portion of the outer section, so as to negate at least a portion of any expansion differences.

In still further aspects of the invention, the supporting member includes a plurality of contact pads, and the system further includes a cable for connecting to a fetal monitor at one end thereof, a plurality of connectors extending from the opposite end of the cable and secured to the plurality of contact pads, and a plurality of wires extending from the sensing member to the contact pads. The plurality of connectors may each comprise solid unstranded telephone cable, and the cable which is connectable to the fetal monitor may include an extended venting lumen for enabling venting therethrough, and for enabling underwater use thereof. Solid wire makes it less labor intensive to solder to the contact pads, as there is no twisting and trimming of strands.

In accordance with other aspects of the invention, the plurality of connectors in the cable which is connectable to the fetal monitor are able to be soldered directly to the contact pads, for providing a secure connection thereof.

In other aspects of the invention, the opposed ends of the extending portions of the supporting element include slots and posts, and the securing element includes opposed ends and has buttonholes. The opposed ends of the securing element are able to extend directly over the post, and each of the buttonholes is able to stretch over and interlock with the post to engage therewith for securing the system about the abdomen.

In another aspect of the invention, the opposed ends of the extending portions of the supporting element include slots, and the securing element includes opposed ends, each of which includes interengageable elements. The opposed ends of the securing element are able to extend through the slots in the opposed ends of the extending portions and fold thereover, and the interengageable elements are able to interengage for securing thereof.

In still other aspects of the invention, the system further includes a cover, for covering the supporting member, the sensing member, and a portion of the cable which is connectable to the fetal monitor. The cover includes a pair of posts, one on each of the opposed ends thereof, the securing element includes opposed ends, and has buttonholes, and each of the buttonholes in the securing element is able to stretch over and interlock with one of the posts to engage therewith for securing the system about the abdomen.

These and other aspects and advantages of the invention will become apparent from the following detailed description and the accompanying drawings, which illustrate by way of example the features of the invention.

BRIEF DESCRIPTION OF THE DRAWINGS

FIG. 5 is an elevational partly sectional view of a pressure sensor, a force collector, and a supporting element in the sensing system;

FIG. 6 is an elevational cross-sectional view of a pressure sensor and a force collector in the sensing system;

FIG. 7 is an elevational partly fragmentary view of the system including a ridge area in the supporting element;

FIG. 8 is an elevational partly fragmentary view of the system including a counterbore area in the supporting element;

DETAILED DESCRIPTION OF THE PREFERRED EMBODIMENTS

Figure 1:
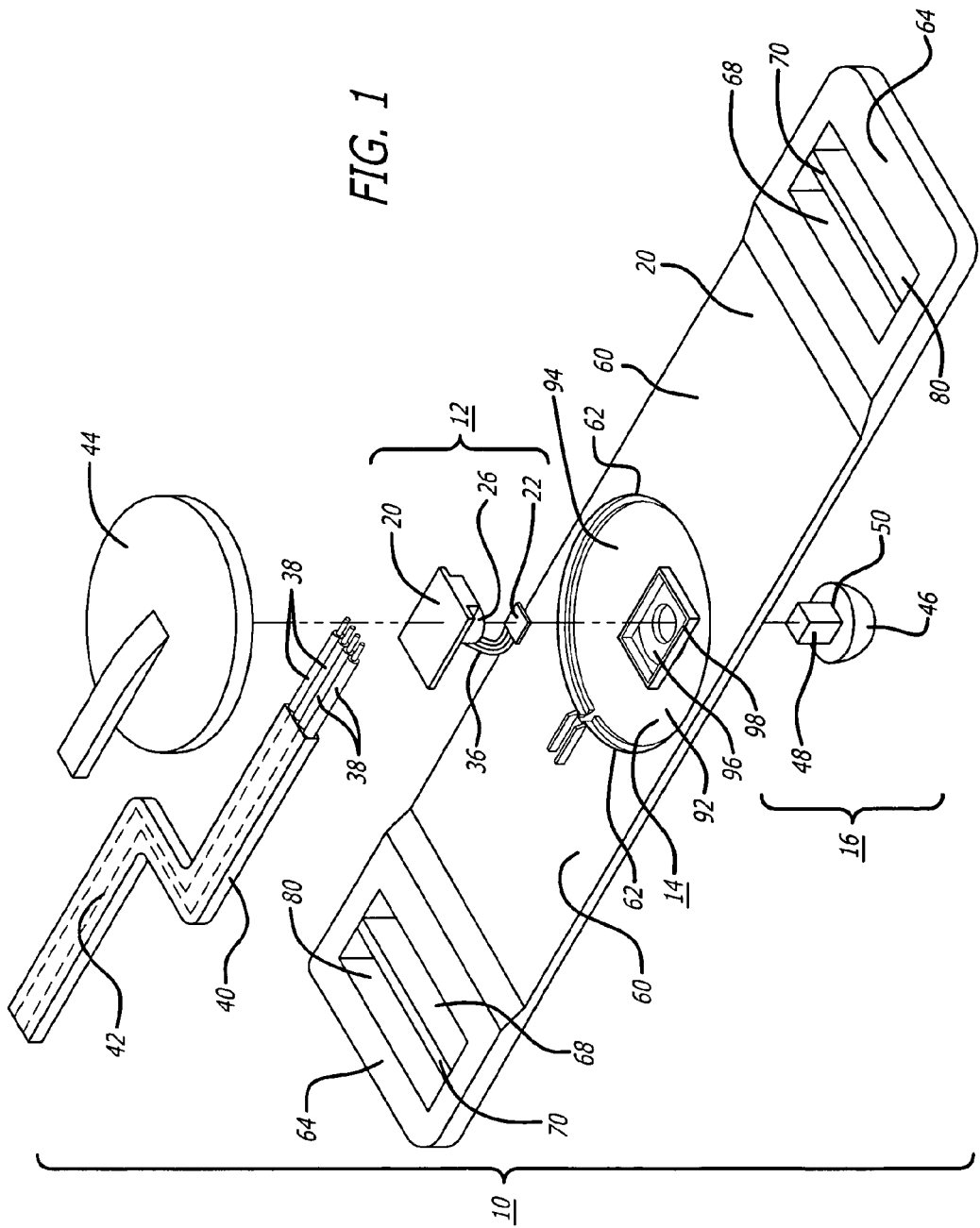
FIG. 1 is an exploded top perspective view of a sensing system in accordance with aspects of the present invention.

Referring to the drawings, in which like reference numerals refer to like or corresponding parts, the system according to the invention senses the frequency and duration of uterine contractions during labor and estimates the relative intensity thereof. The system is able to sense changes in pressure in response to uterine muscle tone changes relating to contractions, and to enable a fetal monitor to be connected thereto for evaluation of contractions.

Figure 3:
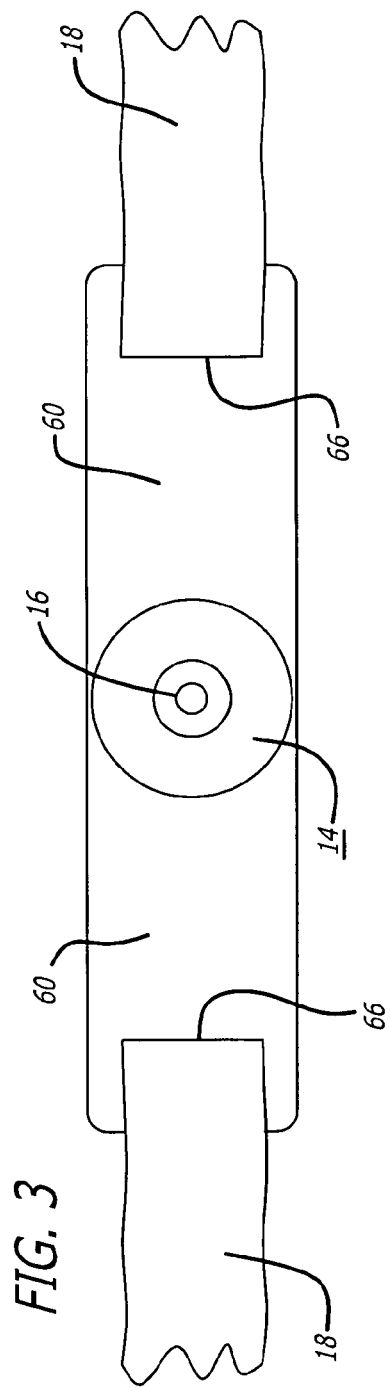
FIG. 3 is a bottom partly fragmentary plan view of the sensing system.
Figure 4:
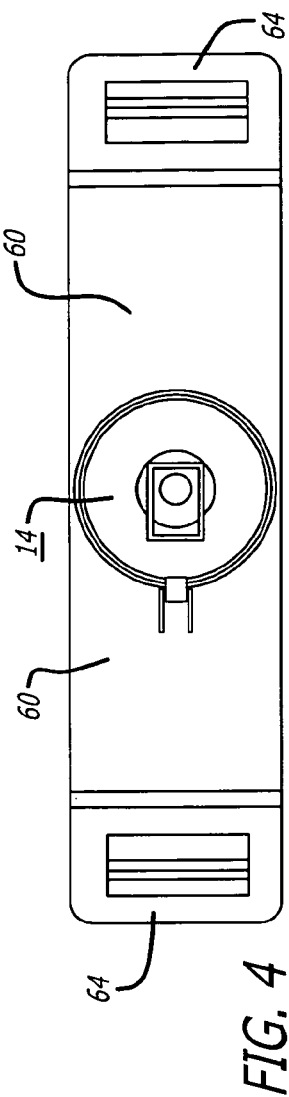
FIG. 4 is a top plan view of a pressure sensor and a supporting element in the sensing system.

FIG. 1 presents a sensing system 10 in accordance with the invention, which enables the sensing and monitoring of uterine contractions. The sensing system 10 according to the invention includes a pressure sensor 12, for sensing changes in pressure responsive to uterine muscle tone changes. The pressure sensor 12 is positionable against the exterior abdominal wall proximate the uterine muscle, and is connectable to a fetal monitor for evaluation of contractions during labor. It is supportable so as to project into the abdominal wall to reside at least partially below the non-compressed surface of the abdomen. The system 10 further includes a supporting element 14, for supporting the pressure sensor 12, such that the pressure sensor 12 projects into the abdominal wall to reside at least partially below the non-compressed surface of the abdomen. Also, the system includes a force collector 16, secured to the pressure sensor 12 so as to bear against the exterior abdominal wall proximate the uterine muscle. The force collector 16 projects into the abdominal wall to reside at least partially below the non-compressed surface of the abdomen. The force collector 16 moves responsive to uterine muscle tone changes, as by displacing or compressing so as to exert pressure responsive thereto relative to the pressure sensor 12. Further, as seen in FIG. 3, the system includes a securing element 18, for enabling the securing of the pressure sensor 12, the supporting element 14, and the force collector 16 in position against the exterior abdominal wall proximate the uterine muscle.

The pressure sensor 12 is generally small and lightweight, and the supporting element 14 is generally low profile and lightweight. The pressure sensor 12 is further able to be actuated by an excitation voltage from a fetal monitor, and to send a signal voltage back to the fetal monitor responsive to changes in pressure. The pressure sensor 12 may comprise a piezo-resistive pressure sensor. It includes a supporting member 20, and a sensing member 22 for sensing changes in pressure responsive to uterine muscle changes relating to contractions, and for enabling a fetal monitor to be connected thereto. The sensing member 22 is supported in the supporting member 20.

There is shown in FIG. 6 a cross-sectional view of the supporting member 20 which is able to be formed as a supporting part, and which is extendable between the pressure sensor 12 and the supporting element 14. The supporting member 20 may for example include a gel cup 24 which includes a wall portion 26, and a base portion 28. The gel cup 24 is comprised of generally molded plastic material, and is able to be filled with a non-conductive silicone gel to form a portion of the force collector 16. The supporting member 20 further includes a bonding element 30, for bonding the force collector 16 to the gel cup 24, and a ceramic chip substrate 32. The supporting member 20 may alternatively for example comprise a gel cup 24, comprised of generally molded plastic material, and a ceramic chip substrate 32, or for example may comprise a ceramic chip substrate 32.

Figure 2:
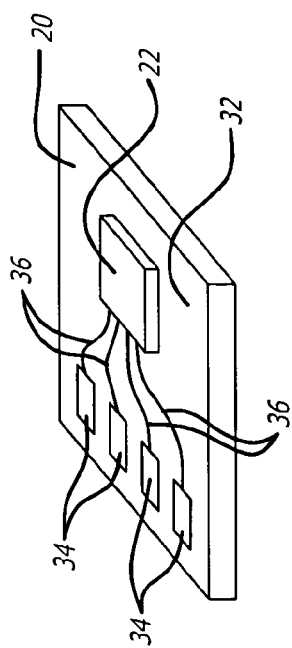
FIG. 2 is a bottom perspective view of a sensing member, wires, and contacts in a supporting member.

Referring to FIG. 2, the supporting member 20 includes a plurality of contact pads 34. A plurality of wires 36 connect the sensing member 22 to the contact pads 34. In the event of the application of a voltage or current exceeding a limit, the wires 36 connecting the sensing member 22 to the contact pads 34 will fail substantially instantaneously, preventing current from flowing to the patient. The contact pads 34 further are able to receive a plurality of connectors 38, as seen in FIG. 1, which extend in a cable 40 for a fetal monitor. Some baby deliveries are performed in water, requiring a system which is waterproof, as it may be submerged. The sensing member 22 is referenced to atmospheric pressure for proper pressure measurement, whereby for such deliveries a vent is required, which is provided though the cable 40. The plurality of connectors 38 in the cable 40 may each comprise solid strand telephone cable, and the cable 40 may include an extruded venting lumen 42 for enabling venting therethrough, and for enabling underwater use thereof. The plurality of connectors 38 in the cable 40 may be soldered directly to the contacts pads 34 in the sensing element 12, for providing a secure connection thereto. The system 10 also includes a cover 44, for covering the supporting member 20, the sensing member 22, and a portion of the fetal monitor cable 40.

The sensing member 22 is supported in the supporting member 20 such that the sensing member 22 is able to project into the abdominal wall to reside at least partially below the non-compressed surface of the abdomen. The sensing member 22 comprises the active area of the pressure sensor 12. It includes resistors, which may comprise for example thin film resistors deposited thereon, which resistors are able to change the resistance with changes in applied pressure. The resistors in the sensing member 22 may comprise a balanced resistor network, which may comprise a silicon semiconductor Wheatstone bridge. The sensing member 22 and the supporting member 20 for example may comprise a pressure transducer. Alternatively for example the sensing member 22 and a supporting portion of the supporting element 20 may comprise a pressure transducer, or for example the sensing member 22 and a supporting part of the supporting element 20 may comprise a pressure transducer. The ceramic chip substrate 32 of the supporting member 20 may include compensating resistors therein, for providing compensation for the resistors in the sensing member 22.

As further illustrated in FIG. 6, the force collector 16, which is able to interact with the sensing member 22 by displacing or compressing so as to exert pressure on the sensing member 22 responsive to uterine muscle tone change, is supported in the supporting member 20. The force collector 16 is formed of a material which is able to be dispensed and formed relative to the gel cup 24. The gel cup 24 includes the bonding element 30 for providing an adhering portion, to enable the material of which the force collector 16 is formed to adhere thereto. The force collector 16 includes an outer section 46, an inner section 48, and an interface 50 (FIG. 1) between the outer section 46 and the inner section 48. The supporting member 20 supports the sensing member 22 and the inner section 48 of the force collector 16 therein, and supports the outer section 46 of the force collector 16 thereon. The outer section 46, which may be comprised for example of an ultraviolet-cured flexible adhesive, projects from the supporting element 14. The inner section 48 is comprised of compliant material, for example a silicone gel, and contacts the sensing member 22. The force collector 16 projects from the supporting element 14 and is moveable therein. The supporting member 20 and the inner section 48 of the force collector 16 are further able to support the pressure sensor 12 so as to isolate the pressure sensor 12 from the external environment, to prevent current from flowing to the patient. The compliant material of the inner section 48 of the force collector 16 is able to be formed in the wall portion 26, on the base portion 28 of the gel cup 24 and the ceramic chip substrate 32, and over and about the piezo-resistive pressure sensor 12.

The force collector 16 is generally in the shape of a nipple, and may be comprised of a generally soft and compliant material. The generally compliant material of which the force collector 16 is comprised for example may be a generally compliant polymer material, a generally compliant monomer material, or another generally compliant material such as latex. The force collector 16 may alternatively for example be comprised of a generally non-compliant material which includes compliant material therein, such as an oil. The generally compliant material and the generally non-compliant material may comprise a generally soft low durometer material or a generally non-low durometer non-compliant material. The system 10 may include a protective cover 52, which extends over the force collector 16 to provide additional protection for the generally low durometer embodiment of the force collector 16. The protective cover 52 may be thin, may be comprised of polyethylene, and may have a vent hole 54 therein, for enabling the venting of trapped air therethrough. The protective cover 52 also enables the force collector 16 to slide over the patient's skin, and prevents the force collector 16 from sticking to the patient's skin, when the clinician wishes to reposition the system 10. The vent hole 54 prevents the air from expanding as it warms up on the patient's abdomen, which may otherwise cause a zero shift in the pressure reading. The protective cover 52 is also able to prevent sticking of the force collector 16, which might otherwise pull on the force collector 16 causing negative pressure readings when the protective cover 16 is unloaded and returns to its natural state.

An outer section-inner section ratio comprises the ratio of the linear width of the force collector outer section 46 to the linear width of the force collector inner section 48. The width of the linear width of the outer section 46 of the force collector 16 comprises the linear widest width thereof. The ratio for example is no greater than about three and one-half to one, and may be about two and one-half to one. An interface-inner section ratio comprises the ratio of the cross-sectional area of the width of the force collector interface 50 to the cross-sectional area of the width of the force collector outer section 46. The interface-inner section ratio of the interface 50 of the force collector 16 to the outer section 46 of the force collector 16 is substantially minimal. The interface-inner section ratio may comprise the ratio of the cross-sectional area of the width of the interface 50 to the cross-sectional area of the width of the inner section 48. The cross-sectional area of the width of the force collector 16 comprises the cross-sectional area of the widest width thereof. The ratio for example is no greater than about eight to one, and may be about four to one.

The coefficient of thermal expansion of the solid non-fluid outer section 46 of the force collector 16 is substantially similar to the coefficient of thermal expansion of the solid non-fluid inner section 48 of the force collector 16. If there is a difference in the coefficient of thermal expansion between the outer section 46 and the inner section 48 of the force collector 16, a zero shift in the pressure reading may result as the system 10 warms on the patient's skin. The average thickness of an outer portion 56 of the outer section 46 of the force collector 16 is less than the average thickness of an inner portion 58 of the outer section 46 of the force collector 16, to additionally help to overcome slight differences in coefficients of thermal expansion of the outer section 46 and the inner section 48 of the force collector 16. The outer portion 56 of the outer section 46 is retained firmly against a non-moving surface, thereby keeping the thickness of the outer section 46 down in this area, and allowing the inner portion 58 of the outer section 46 to move more freely over the inner section 48, so as to negate at least a portion of any expansion differences.

The pressure sensor 12 is able to be formed such that ratios of the pressure sensor 12 relative to the force collector 16 are substantially minimal so as to maximize the sensitivity of the system 10. An inner section-sensing member ratio of the inner section 48 of the force collector 16 to the sensing member 22 of the pressure sensor 12 is substantially minimal. The inner section-sensing member ratio comprises the ratio of the area of the width of the force collector inner section 48 to the width of the sensing member 22. The width of the force collector inner section 48 and the width of the sensing member 22 comprises the width in any direction thereof. The ratio for example is no greater than about three and one-half to one, and may be about two and one half to one. Alternatively, the inner section-sensing member ratio comprises the ratio of the area of the force collector inner section 48 to the area of the sensing member 22. The ratio for example is no greater than about eight to one, and may be about live to one.

The securing element 18 for example comprises a belt, which is comprised of generally elastic material. The generally elastic material may for example comprise an elastic nylon material, or an elastic polyester material. The supporting element 14 also leverages the pressure sensor 12, so as to enable the securing element 18 to load the pressure sensor 12 onto the abdomen, with substantially minimal retention pressure exerted by the securing element 18 on the pressure sensor 12. Further, the supporting element 14 is comprised of a flexible material or a non-flexible material, such that, in conjunction with the securing element 18, the flexible material or the non-flexible material maintains a load on the pressure sensor 12 during abdominal changes in response to contractions. The flexible material of which the supporting element 14 may be comprised is preferably a flexible plastic material, which flexible plastic material may constitute for example a thermoplastic such as polycarbonate.

In the embodiment as seen in FIGS. 1, 3-5, and 7-8, the supporting element 14 further includes extending portions 60 which extend from the opposed sides 62 of the supporting element 14, which extending portions 60 include opposed ends 64, to which opposed ends 66 of the securing element 18 are attachable, to provide leverage for the force collector 16. The extending portions 60 include the opposed ends 64, attachment portions 68 at the opposed ends 64 thereof, and an attachment point 70 at which the attachment portions 68 enable the securing element 18 to secure the system 10 about the abdomen. The attachment point 70 is a distance from the force collector 16 such that the extending portions 60 including the attachment portions 68 thereof leverage the force collector 16. The leveraging provided by the extending portions 60 including the attachment portions 68 is sufficiently flexible to deflect with the tension exerted by the securing element 18 thereon, so that the supporting element 14 conforms to the natural curvature of the abdomen. The force collector 16 includes edges 72 thereof, and a leveraging ratio of the distance from the attachment points 70 through the edges 72 of the force collector 16, to the width of the force collector 16, is greater than 1.5 to 1, and may be greater than 13 to 1.

The supporting element 14 may include an inhibiting portion 74, comprising a ridge area 76, as seen in FIG. 7, or a counterbore area 78, as shown in FIG. 8, each of which comprises a detail such as a meniscus, and which is formed relative to the bonding element adhering portion 30, for inhibiting the material of which the force collector 16 is formed from flowing beyond the adhering portion 30, so as to prevent the material from affecting the sensitivity of the system. The sensitivity of the active area in the sensing member 22 is affected by the extent of the force collector 16 which is supported thereon which extends beyond the width of the sensing member 22 and is outside the active area thereof. The inhibiting portion 74 reduces the relative surface tension of the supporting element 20 therebeyond for the nipple material of the force collector 16, so as to resist the nipple material from flowing therebeyond. The ridge area 76 in FIG. 7, for example, may be about 0.005 inches high by 0.010 inches wide.

Figure 9:
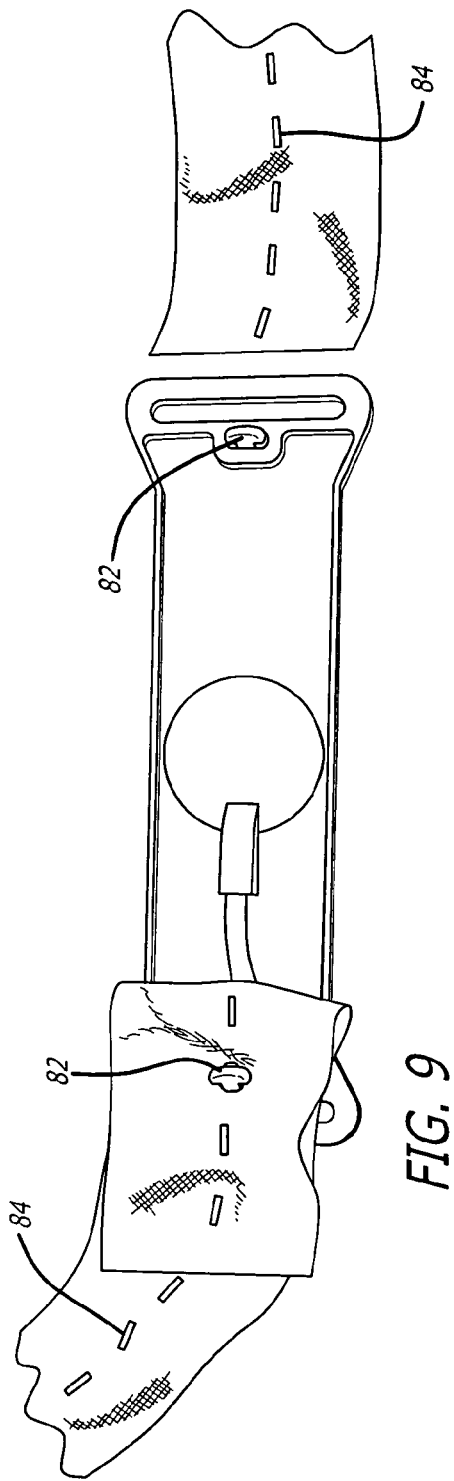
FIG. 9 is an elevational view of a supporting element and a securing element in accordance with aspects of the present invention.

In the embodiment shown in FIG. 9, the opposed ends 64 of the extending portions 60 of the supporting element 14 include slots 80 and posts 82, and the securing element 18 may have buttonholes 84 therein, the opposed ends 66 of the securing element 18 are able to extend through the slots 80 in the opposed ends 64 of the extending portions 60 and fold thereover, and wherein each of the buttonholes 84 is able to stretch over and interlock with the post 82 to engage therewith for securing the system 10 about the abdomen. Alternatively, the securing element 18 may include interengageable elements whereby the opposed ends of the securing element 18 extend through the slots 80 and fold back thereover, such that the interengageable elements interengage for securing thereof.

Figure 10:
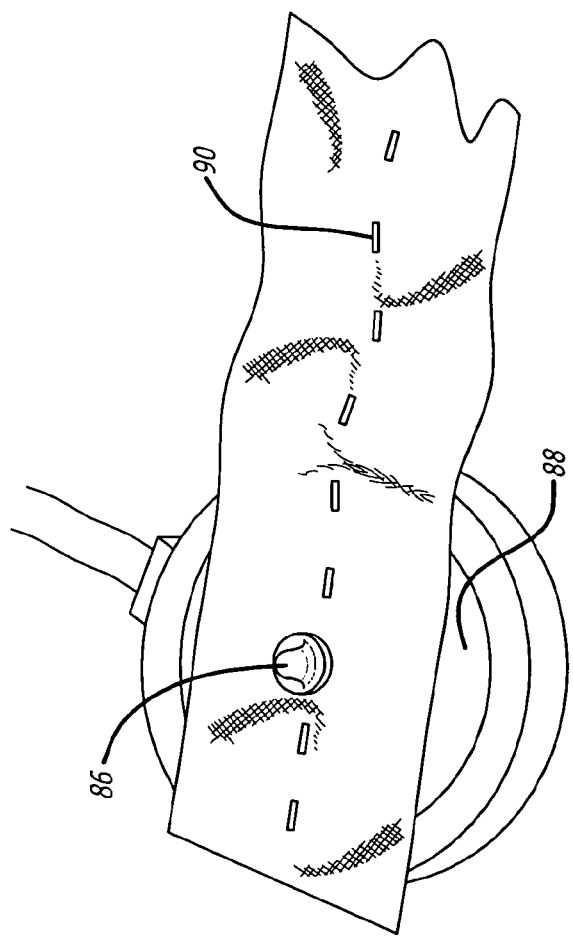
FIG. 10 is a perspective view of a cover for the supporting element and a securing element.

The FIG. 10 embodiment illustrates the cover 44 which includes a post 86 on its outer surface 88, and wherein the securing element 18 may have buttonholes 90 therein, wherein each of the buttonholes 90 is able to stretch over and interlock with the post 86 to engage therewith, for securing the system 10 about the abdomen. In this embodiment, the supporting element 14 does not include extending portions 60.

The supporting element 14 is generally low profile and lightweight. It includes a housing 92 which includes a mounting portion 94 for mounting the pressure sensor 12 therein, is generally semi-spherical in shape, generally in the form of a dome, and includes a recess 96 in the form of a well therein. The pressure sensor 12 is able to project from and be moveable in the recess 96 of the supporting element 14. The housing 92 further includes a generally rectangular-shaped back portion 98 from which the mounting portion 94 projects.

The supporting element 14 may be is comprised of a flexible or non-flexible material, such that the flexible or non-flexible material maintains a load on the pressure sensor 12 during abdominal changes relating to contractions. The flexible material may comprise a flexible plastic material.

While the particular sensing system as shown and disclosed in detail herein is fully capable of obtaining the objects and providing the advantages previously stated, it is to be understood that it is merely illustrative of the presently preferred embodiment of the invention, and that no limitations are intended to the details of construction or design shown herein other than as described in the appended claims.

We claim:

1. A system for sensing the frequency and duration of uterine contractions during labor and estimating the relative intensity thereof, able to sense changes in pressure in response to uterine muscle tone changes relating to contractions, and to enable a fetal monitor to be connected thereto for evaluation of contractions, comprising:

a force collector, for collecting force generated in response to uterine muscle tone changes relating to contractions, positionable against the exterior abdominal wall proximate the uterine muscle, and supportable so as to project into the abdominal wall to reside at least partially below the non-compressed surface of the abdomen;

a pressure sensor, for sensing changes in pressure in the force collector responsive to uterine muscle tone changes, positionable adjacent to the force collector which is positionable against the exterior abdominal wall proximate the uterine muscle, which pressure sensor is supportable so as to project into the abdominal wall to reside at least partially below the non-compressed surface of the abdomen, and is connectable to a fetal monitor for evaluation of contractions during labor, which includes a supporting member, which includes a plurality of contact pads, and the system further comprises a cable for connecting to a fetal monitor at one end thereof, a plurality of connectors extending from the opposite end of the cable and secured to the plurality of contact pads, and a plurality of wires extending from the sensing member to the contact pads, and a sensing member for sensing changes in responsive to uterine muscle changes relating to contractions, supportable in the supporting member so as to project into the abdominal wall to reside at least partially below the non-compressed surface of the abdomen, and connectable to a fetal monitor for evaluation of contractions during labor; and a supporting element, for supporting the force collector so as to be positionable against the exterior abdominal wall proximate the uterine muscle and for supporting the pressure sensor adjacent to the force collector, and for supporting the force collector and the pressure sensor such that the force collector and the pressure sensor projects into the abdominal wall to reside at least partially below the non-compressed surface of the abdomen.

2. A system as in claim 1, wherein the plurality of connectors each comprise solid strand telephone cable.

3. A system as in claim 1, wherein the plurality of connectors in the cable are able to be soldered directly to the contact pads.

4. A system for sensing the frequency and duration of uterine contractions during labor and estimating the relative intensity thereof, able to sense changes in pressure in response to uterine muscle tone changes relating to contractions, and to enable a fetal monitor to be connected thereto for evaluation of contractions, comprising:

a force collector, for collecting force generated in response to uterine muscle tone changes relating to contractions, positionable against the exterior abdominal wall proximate the uterine muscle, and supportable so as to project into the abdominal wall to reside at least partially below the non-compressed surface of the abdomen;

a pressure sensor, for sensing changes in pressure in the force collector responsive to uterine muscle tone changes, positionable adjacent to the force collector which is positionable against the exterior abdominal wall proximate the uterine muscle, which pressure sensor is supportable so as to protect into the abdominal wall to reside at least partially below the non-compressed surface of the abdomen, and is connectable to a fetal monitor for evaluation of contractions during labor, which includes a supporting member, and a sensing member for sensing changes in pressure responsive to uterine muscle changes relating to contractions, supportable in the supporting member so as to project into the abdominal wall to reside at least below the non-compressed surface of the abdomen, and connectable to a fetal monitor for evaluation of contractions during labor, wherein the supporting member comprises a gel cup, comprised of generally molded plastic material, a bonding element for bonding the sensing member thereto, and a ceramic chip substrate, and wherein the gel cup is comprised of compliant material which comprises a non-conductive silicone gel, which fills the gel cup; and a supporting element, for supporting the force collector so as to be positionable against the exterior abdominal wall proximate the uterine muscle and for supporting the pressure sensor adjacent to the force collector, and for supporting the force collector and the pressure sensor such that the force collector and the force collector and the pressure sensor projects into the abdominal wall to reside at least partially below the non-compressed surface of the abdomen.

5. A system as in claim 4, wherein the compliant material of the force transmitting member is able to be dispensed and formed relative to the gel cup, the gel cup includes an adhering portion, able to enable the compliant material to adhere thereto, and the supporting element includes an extending portion, which is formed relative to the adhering portion, and which is able to inhibit the compliant material of the force transmitting member from flowing beyond the adhering portion.

6. A system as in claim 4, wherein the ceramic chip substrate includes compensating resistors.

7. A method of sensing the frequency and duration of uterine contractions during labor and estimating the relative intensity thereof, able to sense changes in pressure in response to uterine muscle tone changes relating to contractions, and to enable a fetal monitor to be connected thereto for evaluation of contractions, in a system which comprises a force collector, for collecting force generated in response to contractions, positionable against the exterior abdominal wall proximate the uterine muscle, and supportable so as to project into the abdominal wall to reside at least partially below the non-compressed surface of the abdomen, a pressure sensor, for sensing changes in pressure in the force collector responsive to uterine muscle tone changes, positionable adjacent the force collector which is against the exterior abdominal wall proximate the uterine muscle, supportable so as to project into the abdominal wall to reside at least partially below the non-compressed surface of the abdomen, and is connectable to a fetal monitor for evaluation of contractions during labor, and a supporting element, for supporting the force collector so as to be positionable against the exterior abdominal wall proximate the uterine muscle and for supporting the pressure sensor adjacent the force collector, and for supporting the force collector and the pressure sensor such that the force collector and the pressure sensor projects into the abdominal wall to reside at least partially below the non-compressed surface of the abdomen, wherein the method comprises;

collecting force generated in response to uterine muscle tone changes relating to contractions, in the force collector which is positionable against the exterior abdominal wall proximate the uterine muscle, and which is supportable so as to project into the abdominal wall to reside at least partially below the non-compressed surface of the abdomen;

sensing changes in pressure in the force collector responsive to uterine muscle tone changes, in the pressure sensor which is positionable adjacent to the force collector which is positionable against the exterior abdominal wall proximate the uterine muscle, which pressure sensor is supportable so as to project into the abdominal wall to reside at least partially below the non-compressed surface of the abdomen, and is connectable to a fetal monitor for evaluation of contractions during labor; and supporting the force collector in the supporting element so as to be positionable against the exterior abdominal wall proximate the uterine muscle and for supporting the pressure sensor adjacent to the force collector, and for supporting the force collector and the pressure sensor such that the force collector and the pressure sensor projects into the abdominal wall to reside at least partially below the non-compressed surface of the abdomen.

8. A method as in claim 7, wherein the pressure sensor includes a supporting member, and a sensing member for sensing changes in pressure responsive to uterine muscle changes relating to contractions, supportable in the supporting member so as to project into the abdominal wall to reside at least partially below the non-compressed surface of the abdomen, and connectable to a fetal monitor for evaluation of contractions during labor, and wherein supporting in the method further comprises supporting the sensing member in the supporting member, and sensing further comprises sensing pressure changes by the sensing member, and the method further comprises enabling a fetal monitor to be connected to the sensing member.

9. A method as in claim 7, wherein the pressure sensor is generally small and lightweight, and the supporting element is generally low profile and lightweight, and wherein supporting in the method further comprises supporting the generally small and lightweight pressure sensor by the generally low profile and lightweight supporting element and wherein sensing in the method further comprises sensing by the generally small and lightweight pressure sensor.

10. A method as in claim 7, wherein the pressure sensor is further able to be actuated by an excitation voltage from a fetal monitor, and to send a signal voltage back to the fetal monitor responsive to changes in pressure, and wherein the method further comprises actuating the pressure sensor by an excitation voltage from the fetal monitor, and sending a signal voltage from the pressure sensor back to the fetal monitor responsive to changes in pressure.

* * * * *